Figures 1, 2, 3, 4, 5, 6, 7, 8, 9, 10, 11, 12, 13, 14:
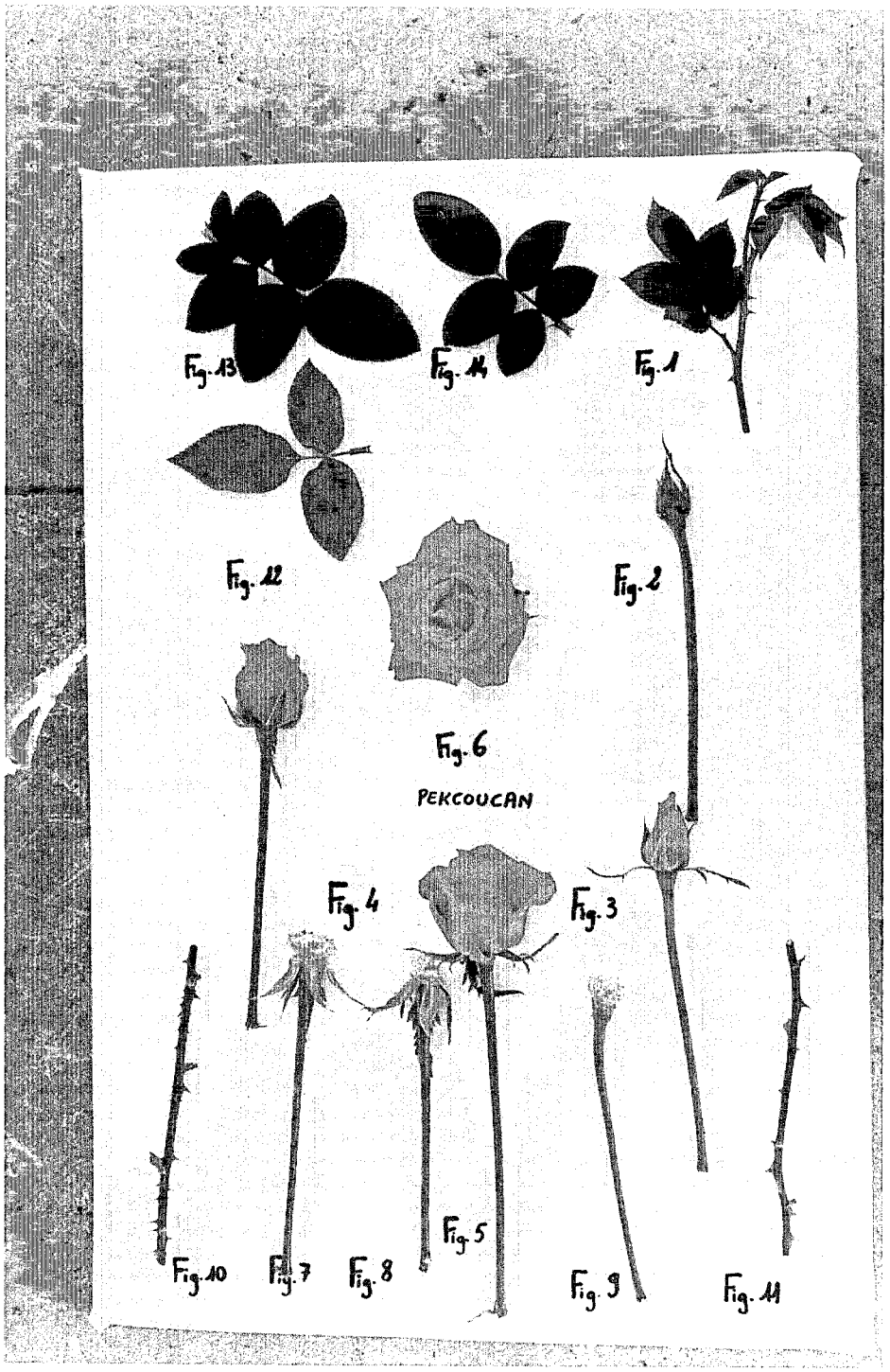

US00PP08280P

United States Patent [19]

Pekmez

[11] Patent Number: Plant 8,280

[45] Date of Patent: Jun. 29, 1993

[54] ROSE PLANT NAMED PEKCOUCAN

[76] Inventor: Paul Pekmez, La Petite Pierre, 67290 Wingen-Sur-Moder, France

[21] Appl. No.: 813,149

[22] Filed: Dec. 23, 1991

[51] Int. Cl.[5] ..... A01H 5/00

[52] U.S. Cl. ..... Plt./20

[58] Field of Search ..... Plt./20, 11, 16, 17, Plt./28

*Primary Examiner*—Howard J. Locker

*Attorney, Agent, or Firm*—Christie, Parker & Hale

[57] ABSTRACT

A new rose plant producing orange red flowers.

1 Drawing Sheet

SUMMARY OF THE INVENTION

The present invention relates to a new and distinct variety of rose plant producing hybrid tea type flowers rose class which was originated by my crossing as seed parent the variety known as 'Pekom Ecli' and as pollen parent the variety known as 'Korpek'. The varietal denomination of this new rose is 'Pekcoucan'.

Among the novel characteristics possessed by this new variety which distinguishes it from its parents and all other varieties of which I am aware are its attractive well formed orange red flowers borne on a plant suitable for cut flower production and for growing outdoors in gardens. Flowers open well and hold their coloring as blooms age. Asexual reproduction by propagation by budding of the new variety as performed in La Petite Pierre, Wingen-Sur-Moder, France, shows that the foregoing and other distinguishing characteristics some true to form and are established and transmitted through succeeding propagations.

BRIEF DESCRIPTION OF ILLUSTRATION

The accompanying illustration shows typical specimens of the vegetative growth and flowers of the new variety in different stages of development and depicted in color as nearly true as it is reasonably possible to make the same in a color illustration of this character. As can be ssen there is described a young stem shoot 1, green bud 2, buds showing color 3 and 4, opening flower 5, open flower 6, reproductive organs 7, 8 and 9, stems with prickles and thorns 10 and 11, and compound 3,7 and 5 leaflet leaves 12, 13 and 14.

DESCRIPTION OF THE NEW VARIETY

Pekcoucan is an unusually fine hybrid tea rose of orange red flower coloration. It may be used in gardens and for cut flower production under glass. The buds are well shaped and of good form and the flowers are 3 to 4 cm. in size.

The following is a detailed description of my new variety, with color terminology in accordance with The Royal Horticultural Society Colour Chart (R.H.S.C.C.). The terminology used in color description herein refers to plate numbers in the aforementioned color chart.

Parentage: Seedling.

*Seed parent.*—'Pekom Ecli'.

*Pollen parent.*—'Korpek'.

The following information is from observations made of specimens grown outdoors in La Petite Pierre, France.

FLOWER

Blooming habit: Recurrent.

A. Bud:

(1) *Size.*—Small to medium.

(2) *Form.*—Ovate.

(3) *Color.*—As sepals divide, bud color is from near 47A to 44A.

(4) *Sepals.*—Longer than bud, foliaceous.

(5) *Peduncle.*—Length: Long in proportion to bloom. Aspect: Straight. Strength: Erect. Color: Near 138B to A.

B. Bloom:

(1) *Size.*—Average size when fully expanded — about 3 to 4 cm.

(2) *Borne.*—Singly, one to a stem.

(3) *Form.*—High centered at first, becoming flat. Petals roll under.

(4) *Petalage.*—Number of petals under normal conditions — about 33 to 43.

(5) *Color.*—After sepals fall and petals unfurl, predominant flower color viewing petals' top surface is orange red, from near 44A to 42A, B. Color of petal undersurface is essentially similar.

C. Petals:

(1) *Texture.*—Medium to thick.

(2) *Appearance.*—Inside velvety and outside satiny.

(3) *Form.*—Broad, fan shaped with some indentation or undulation at margin.

(4) *Arrangement.*—Regularly arranged, imbricated.

(5) *Petaloids in center.*—Few.

(6) *Persistence.*—Petals persist and flowers open slowly.

(7) *Fragrance.*—Slight to none.

(8) *Lasting quality.*—Long lasting on plant and after cutting.

REPRODUCTIVE ORGANS

A. Stamens, filaments and anthers:

*Arrangement.*—Regularly arranged around styles.

*Color.*—Orange yellow.

B. Pollen:

*Color.*—Light yellow.

C. Styles: Medium length.

D. Stigmas:

*Color.*—Orange red.

E. Hips: None observed.

PLANT

A. Form: Upright.

B. Growth: Vigorous.

*Height attained.*—About 50 to 70 cm.

C. Foliage: Compound 3, 5 and 7 leaflets.

(1) *Size.*—Medium.

(2) *Quantity.*—Abundant.

(3) *Color.*—New foliage: Upper side — purple to reddish green. Under side — reddish green to green. Old foliage: Upper side — near 137A. Under side — near 138B.

(4) *Shape.*—Oval, pointed, acuminate.

(5) *Texture.*—Leathery; upper side is semi-glossy; under side is matte.

(6) *Edge.*—Serrate.

(7) *Serration.*—Ordinary.

(8) *Leaf stem.*—Color — medium green.

(9) *Stipules.*—Medium length, simple, short auricle.

(10) *Resistance to disease.*—Mildew — Good.

D. Wood:

(1) *New wood.*—Color — brownish green. Bark — smooth.

(2) *Old wood.*—Color — medium green. Bark — smooth.

E. Thorns:

*Quantity (main stalk).*—Numerous.

*On laterals from stalk.*—Many.

*Form.*—Long, thin, straight, angled downward.

*Length.*—Medium.

*Color.*—Near tan to pink.

*Position.*—Irregular.

*Prickles.*—Regular.

F. Winter hardiness: Needs protection in severe climates.

I claim:

1. A new and distinct variety of rose plant suitable for growing under glass and outdoors, substantially as shown and described.

* * * * *

PEKCOUCAN